US00PP27462P2

(12) United States Plant Patent
Hansen

(10) Patent No.: US PP27,462 P2
(45) Date of Patent: Dec. 13, 2016

(54) ***PHLOX* PLANT NAMED 'OPENING ACT BLUSH'**

(50) Latin Name: ***Phlox* hybrid**
Varietal Denomination: Opening Act Blush

(71) Applicant: Hans A. Hansen, Zeeland, MI (US)

(72) Inventor: Hans A. Hansen, Zeeland, MI (US)

(73) Assignee: Walters Gardens Inc, Zeeland, MI (US)

( * ) Notice: Subject to any disclaimer, the term of this patent is extended or adjusted under 35 U.S.C. 154(b) by 0 days.

(21) Appl. No.: 14/756,746

(22) Filed: Oct. 7, 2015

(51) Int. Cl.
*A01H 5/02* (2006.01)

(52) U.S. Cl.
USPC ..... Plt./320

(58) Field of Classification Search
USPC ..... Plt./320
See application file for complete search history.

*Primary Examiner* — Annette Para

(57) ABSTRACT

A new and distinct plant cultivar of garden *phlox* named *Phlox* 'Opening Act Blush' with sweet-smelling flowers of light lavender-pink flowers on broad strong stems over a long period, that has powdery mildew resistant foliage, especially suitable in the garden as a specimen or en masse, potted plant or patio, for color, fragrance and attracting hummingbirds and butterflies, and for cut flower arrangements.

1 Drawing Sheet

Botanical classification: *Phlox* hybrid.
Variety denomination: 'Opening Act Blush'.

BACKGROUND OF THE NEW PLANT

The present invention comprises a new and distinct variety of hybrid garden *phlox* botanically known as *Phlox* hybrid, and hereinafter referred to by the cultivar name 'Opening Act Blush'. The new variety originated from a crossing made by the inventor on Sep. 1, 2011 at a wholesale perennial nursery in Zeeland, Mich., USA between the female parent *Phlox* 'Minnie Pearl' (not patented) and the male parent *Phlox paniculata* 'Barsixtytwo' U.S. Plant Pat. No. 22,234 with seed harvested Oct. 6, 2011. 'Minnie Pearl' is an interspecific cross between *Phlox maculata* and *Phlox glaberrima*. The new plant was selected from among a large population of as a single individually developed seedling and then separately designated under the breeder code H11-98-56 with final evaluations approved in the summer of 2013.

*Phlox* 'Opening Act Blush' has been asexually propagated by stem cuttings at the same nursery in Zeeland, Mich. The unique characteristics of the new plant have been found to be reproducible and stable in successive generations of asexual propagation and the resultant plants have been found to be identical to the original selection. The present invention has been found to retain its distinctive characteristics through successive asexual propagations via vegetative cuttings.

*Phlox* 'Opening Act Blush' has not been made publically available or sold anywhere in the world under any name more than one year prior to the filing of this application. Any public disclosure or sale has been by the inventor or one who obtained the material either directly or indirectly from the inventor, and any such disclosure has not been made more than one year prior to the application of this invention.

SUMMARY OF THE INVENTION

*Phlox* 'Opening Act Blush' is unique from all other garden *phlox* known to the inventor. The closest comparison variety is *Phlox* 'Barsixtyone' U.S. Plant Pat. No. 22,223. Compared to the new plant, 'Barsixtyone' is slightly shorter, flowers beginning about one week later in the summer and the flower color is darker violet. Compared to the female parent *Phlox* 'Minnie Pearl', the new plant has flowers that are light lavender-pink colored, blooms for a much longer period, and the foliage is longer and wider. The new plant also is has a more compact and less running habit, and has flower petals that are more imbricate than 'Minnie Pearl'. Compared to the male parent, 'Barsixtytwo' is more coral red in flower color, has larger flower panicles with less branching, and does not have the extended bloom period of 'Opening Act Blush'. Table 1 below compares 'Opening Act Blush' with other *Phlox paniculata* and hybrid cultivars of similar flower color. *Phlox* 'Hesperis', 'Ping Pong', 'Fesselballon', 'Franz Schubert', 'Katherine', 'Pinky Hill', 'Rosa Goliath', 'Rowie' 'Swirly Burly', and 'Violetta Gloriosa' are all non-patented plants.

TABLE 1

| CULTIVAR | FLOWER COLOR | FLOWER DIAMETER | BLOOM PERIOD | HEIGHT | MILDEW RESISTANCE |
|---|---|---|---|---|---|
| × *arendsii* 'Hesperis' | lilac purple | 25 mm | mid-Jul-mid-Sept | 75 cm | prone |
| × *arendsii* 'Ping Pong' | light pink | 38 mm | late-Jun-late Jul | 60 cm | prone |
| 'Barsixtyone' | violet | 25 mm | late-Jun-early Sept | 45 cm | good |
| 'Fesselballon' | light lavender, darker eye | 30 mm | late-Jun-early Sept | 100 cm | good |
| 'Franz Schubert' | lavender purple | 30 mm | late-Jul-mid-Sept | 100 cm | poor |
| 'Katherine' | lavender, white eye | 30 mm | late-Jun-mid Sept | 100 cm | good |
| 'Minnie Pearl' | white, no eye | 25 mm | early Jun-late-Aug | 50 cm | excellent |
| 'Opening | light | 24 mm | early-Jun- | 50 cm | excellent |

TABLE 1-continued

| CULTIVAR | FLOWER COLOR | FLOWER DIAMETER | BLOOM PERIOD | HEIGHT | MILDEW RESISTANCE |
|---|---|---|---|---|---|
| Act Blush' | lavender-pink | | early-Oct | | |
| 'Pinky Hill' | light pink, white eye | 32 mm | mid-Jul-mid-Sept | 115 cm | good |
| 'Rosa Goliath' | lavender pink | 38 mm | mid-Jul-mid-Sept | 125 cm | good |
| 'Rowie' | light pink, dark eye | 38 mm | late-Jun-mid Sept | 65 cm | good |
| 'Swirly Burly' | lavender, magenta eye | 25 mm | early-Jul-early-Sept | 60 cm | excellent |
| 'Violetta Gloriosa' | light lavender, white streaked | 45 mm | late-Jun-early Sept | 110 cm | fair |

The new plant 'Opening Act Blush' differs from these cultivars and all other garden *phlox* known to the inventor in the following repeatedly observed traits in combination:

1. Bright-green, powdery mildew-resistant foliage on tall stems 50 cm tall.
2. Early-season, fragrant, lilac-lavender flowers with excellent flower coverage.
3. Long blooming season of numerous, highly branched stems.
4. Hardy, vigorous, short and compact growth habit.

BRIEF DESCRIPTION OF THE DRAWINGS

The photographs of the new plant demonstrate the unique traits of *Phlox* 'Opening Act Blush' and the overall appearance of the plant at two-years old. The colors are as accurate as reasonably possible with color reproductions. Variation in ambient light spectrum, source and direction may cause the appearance of minor variation in color.

DETAILED BOTANICAL DESCRIPTION

Figure 1:
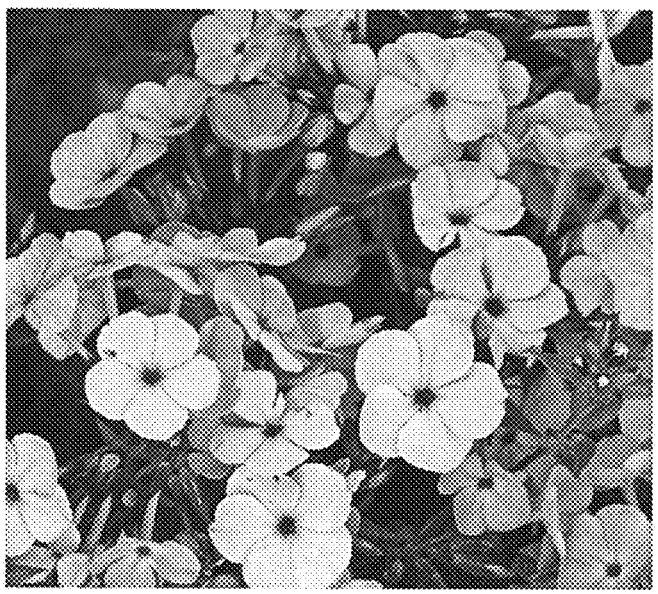
FIG. 1 shows a close-up of the flowers.
Figure 2:
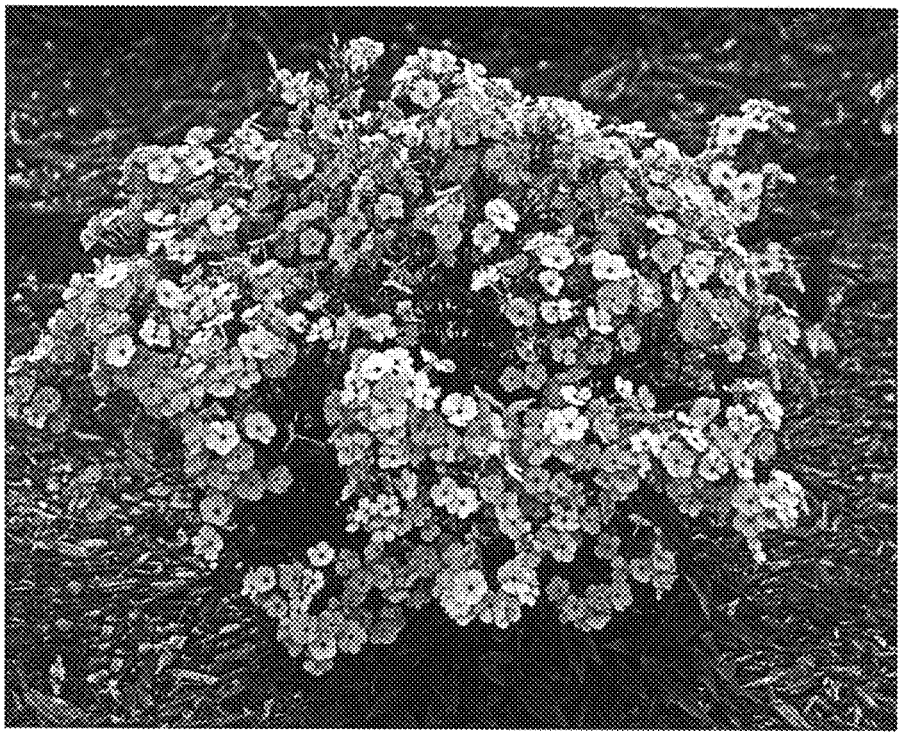
FIG. 2 shows the new plant habit and flowering in an outdoor full-sun display garden in mid-flowering season with clean, disease-free foliage.

The following descriptions and color references are based on the 2001 edition of The Royal Horticultural Society Colour Chart except where common dictionary terms are used. *Phlox paniculata* 'Opening Act Blush' has not been observed under all possible environments. The phenotype may vary slightly with different growing environments such as temperature, light, fertility, soil pH, moisture and maturity levels, but without any change in the genotype. The following observations and size descriptions are based on two-year old plants in the full sun display garden of a wholesale nursery in Zeeland, Mich. with supplemental fertilizer and water as needed and also a partially shaded greenhouse for color comparison, in particular of the flower.

Parentage: Female or seed parent *Phlox* 'Minnie Pearl' (not patented) and the male or pollen parent *Phlox paniculata* 'Barsixtytwo' U.S. Plant Pat. No. 22,234.

Plant habit: Vigorous; mostly upright, bushy with multiple branched stems; about 14 mostly upright stems per plant.

Plant size: About 50.0 cm tall; about 45.0 cm across at widest point (about mid flower height).

Propagation: Stem cuttings.

Time to produce rooted shoots: About 3 weeks.

Time to produce flowering plant: About 4 months during winter and spring season from one-year-old plant; about 12 months from liner starting in mid-summer.

Root description: Fibrous, to about 2.0 mm diameter; root color nearest RHS 158A depending on soil type.

Stems: Mostly upright; rounded in cross section; glabrous; size about 50.0 cm long and 4.0 mm in diameter at base.

Stem color: Upper portion in more shaded vary between RHS 145A and RHS 145C; lower portion and more sun exposed areas between RHS 187C and RHS 184B; stem color at node usually with dark band nearest RHS 187B.

Internode: About 9 before flower branches; average internode length about 2.7 cm, usually greater in distal region.

Branches: Glabrous; four to eight per stem without pinching; upper branches about 10.0 to 18.0 cm long and to about 1.5 mm diameter, lower branches about 15.0 to 22 cm long and 3.0 mm in diameter.

Leaves: Simple, sessile, opposite, oblong elliptic, with acute apex and attenuate base; leaf margin entire; adaxial and abaxial surfaces glabrous; adaxial glossy, abaxial matte; size to about 10.0 cm long and 2.8 cm wide distally smaller, average size about 7.5 cm long and about 2.5 cm wide; number of leaves per flowering stem about 26.

Leaf color: Adaxial surface between RHS 141B and RHS 143B; abaxial surface nearest RHS 138B.

Leaf veins: Pinnate; main vein ridged below and slightly impressed above.

Vein color: Main adaxial nearest RHS 145D at base and nearest RHS 145B toward apex, secondary veins same color as surrounding tissue; abaxial main vein color nearest RHS 147D toward base and darkening to nearest RHS 147C toward apex with secondary veins same color as surrounding tissue.

Flower: Shape salverform; direction facing upright and outwardly; overall length about 2.5 cm, with tube about 19 mm long and five flared petals forming a flattened face to about 24 mm diameter, tube about 2.0 mm diameter at base and about 2.5 mm diameter just below corolla; individual flowers remaining effective for about four days.

Flower fragrance: Sweet.

Petal: Five, complete; smooth and mostly glabrous both adaxial and abaxial; fused together to form a single corolla tube and flattened overlapping blades in face; imbricate to about 2.5 mm of the petals on either side; tube dimensions about 19 mm long about 2.0 mm diameter at base and about 2.5 mm diameter just below corolla; dimension of blade portion about 12.8 mm from tube to apex and about 12.8 mm across in middle; on faded flower eye about 5.8 mm across; tube glabrous inside except densely pubescent band of about 2.5 mm wide and beginning about 3.0 mm from base on inside.

Petal color: Adaxial face nearest RHS 75A; adaxial eye between RHS N74B and RHS N74C; abaxial face between RHS 75C and RHS 75D; adaxial tube nearest RHS 77B; abaxial tube between RHS 77B and RHS 77C; before dropping adaxial flower face lightens to lighter than RHS 75D toward adaxial face perimeter and eye nearest RHS N74C; pubescent band of inner tube middle lighter than RHS N155 C; base of tube nearest RHS 145D.

Sepals: Normally five; glabrous abaxial and adaxial about 8.0 mm long and individually about 1.5 mm wide before being fused in basal 6.5 mm; sharply acute apex and fused base.

Sepal color: Variable with strong light exposure; abaxial color nearest RHS 138C at base and nearest RHS 138A at apex with fusion joints nearest RHS 145D; adaxial nearest RHS 137B at apex and lightening to nearest RHS 137D at base with a 1.0 mm margin along the fusion joint of nearest RHS 145D; with intense light exposure all but the adaxial and abaxial base and fusion joints develops to between RHS N77A and RHS N77B.

Stamens: Five; adnate to inner petal tube, positioned at two heights above base, about 16.0 mm and 13.0 mm.

Filament: Fused to inside of corolla tube; about 1.0 mm long and less than 0.5 mm diameter; color nearest RHS N155B.

Anther: Oblong; dorsifixed; about 2.0 mm long and 0.5 mm diameter; color nearest RHS 11C.

Pollen: Abundant, globose; color between RHS 17A and RHS 17B.

Style: About 18 mm long and less than 0.5 mm diameter; color nearest RHS 139D with slight tinting of nearest RHS N77B lightening to nearest RHS 145D at base.

Stigma: Split in three in the terminal 2.5 mm; color nearest RHS 145D.

Ovary: Ovoid; superior; about 1.5 mm long and 1.0 mm wide tapering to diameter of style in distal portion; apex acute tapering to style; color nearest RHS 145A.

Peduncle: Stiff, strong, cylindrical, glabrous; main flowering portion about 2.5 cm long and about 1.5 mm diameter at base of flowers.

Peduncle color: Upper portion in more shaded region vary between RHS 145A and RHS 145C; lower portion and more sun exposed areas between RHS 187C and RHS 184B.

Pedicel: Glaucous, glabrous, stiff, strong, erect, rounded to about 0.5 cm diameter and to 4.0 mm long.

Pedicel color: Between RHS 137B and RHS 137A with tinting of nearest RHS 187A in tissue exposed to strong light intensity.

Bracts below flower clusters: Simple, sessile, opposite, oblong elliptic, with acute apex and attenuate base; leaf margin entire; adaxial and abaxial surfaces glabrous; adaxial glossy, abaxial matte; average about 30.0 mm long and 10.0 mm across.

Bracts color: Adaxial nearest RHS 146A; abaxial nearest RHS 146C; main adaxial vein nearest RHS 145A, abaxial nearest RHS 147C; abaxial and adaxial secondary veins same color as surrounding tissue.

Fruit: Rare, one to two seeds per longitudinally dehiscent capsule; ovoid; about 5.0 cm long and 3.5 mm diameter; mucronate with apical mucro about 1.5 mm long and 0.5 mm diameter; color at dehiscence nearest RHS 161D.

Seeds: Rare; flattened ellipsoid, about 2.0 mm long, 1.6 mm across and 1.2 mm thick; color mostly between RHS 202A and RHS 200A.

Disease resistance: In side-by-side comparisons *Phlox* 'Opening Act Blush' shows high resistance to powdery mildew, a disease common to many garden *phlox*. Resistance was equal or better than both of the parents. Other disease or pest resistance beyond that which is common to perennial, hardy, garden *phlox* has not been noted.

Hardiness and culture: *Phlox* 'Opening Act Blush' grows best with plenty of moisture and adequate drainage; hardy to at least from USDA zone 4 through 8. *Phlox* 'Opening Act Blush' adds long season beauty and fragrance to the garden and attracts butterflies and hummingbirds.

I claim:

1. A new and distinct plant of hybrid garden *phlox, Phlox* 'Opening Act Blush', as herein described and illustrated.

* * * * *